United States Patent [19]

Wallace et al.

[11] Patent Number: 4,540,833
[45] Date of Patent: Sep. 10, 1985

[54] PROTECTED ETHYNLATED PHENOLS

[75] Inventors: J. Shield Wallace, Dayton; Fred E. Arnold, Centervile, both of Ohio

[73] Assignee: The United States of America as represented by the Secretary of the Air Force, Washington, D.C.

[21] Appl. No.: 592,033

[22] Filed: Mar. 21, 1984

[51] Int. Cl.³ .............................................. C07C 39/11
[52] U.S. Cl. .................................. 568/766; 568/764; 568/794
[58] Field of Search ............... 568/763, 766, 789, 794, 568/764

[56] References Cited

U.S. PATENT DOCUMENTS 3,526,668 9/1970 Starnes, Jr. ........................ 568/780
4,260,832 4/1981 Parker et al. ...................... 568/790

OTHER PUBLICATIONS

Davis et al., "J. Chemical Society", (London), 1959, pp. 3081–3082.

Primary Examiner—Werren B. Lone

Attorney, Agent, or Firm—Donald J. Singer; Charles E. Bricker

[57] ABSTRACT

An acetylenic end-capping agent of the general formula

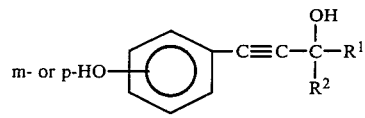

wherein $R^1$ and $R^2$ can be the same or different and are selected from the group consisting of hydrogen, C11 to C4 alkyl, phenyl and substituted phenyl, and wherein $R^1$ and $R^2$ together with the carbon atom to which they are attached form a saturated 5- or 6-membered ring. This end-capping agent is substantially free of Pd and Cu.

Also provided is a method for producing this end-capping agent and a method for producing acetylene terminated compounds.

5 Claims, No Drawings

PROTECTED ETHYNYLATED PHENOLS

RIGHTS OF THE GOVERNMENT

The invention described herein may be manufactured and used by or for the Government of the United States for all governmental purposes without the payment of any royalty.

BACKGROUND OF THE INVENTION

The present invention is directed to α-hydroxy-, α-alkyl-substituted acetylene compounds.

Epoxy matrix composites have been widely used in aerospace products. However, epoxy matrix systems have drawbacks, not the least of which is that such systems are sensitive to moisture. Extended exposure to high humidity reduces the mechanical properties of cured epoxy systems at elevated temperatures. Accordingly, there has been considerable interest in polymers that could replace epoxies and which are significantly less sensitive to moisture, but which retain the desirable characteristics of the epoxies.

A variety of acetylene-terminated resin systems have been prepared and studied in recent years. Acetylene-terminated resins cure through addition rather than condensation, thus avoiding the problem of voids caused primarily by outgassing which occurs during the condensation mechanism cure.

One procedure for adding terminal acetylene groups to an oligomer comprises reacting the oligomer with a substituted terminal acetylene compounds containing at least three carbon atoms with an hydroxy group on the carbon atom adjacent the acetylene group, which may be converted to the desired acetylene terminated oligomer by base catalyzed cleavage. The preparation of acetylene terminated sulfone oligomers by this method is described in U.S. Pat. No. 4,356,325 to Harrison et al. The reaction of the sulfone with the terminal acetylenic compound is carried out in the presence of a palladium salt complex catalyst system and a cuprous salt promoter. A major problem associated with this process is removal of the metallic salts after the displacement reaction. Removal of both Pd and Cu to less than 20 ppm must be accomplished; otherwise premature cross-linking of the acetylene groups can take place leading to poor mechanical performance. Although treatment with a dialkyl or trialkyl-amine does remove these metals in monomeric small molecules, it is extremely difficult to remove the metals from higher molecular weight oligomers.

Another procedure for adding terminal acetylene groups to an oligomer comprises reacting the oligomer with the metallic salt of m-hydroxyphenylacetylene, as disclosed in U.S. Pat. No. 4,108,926 to Arnold et al. The metallic salt is, however, difficult to synthesize and expensive to produce. The synthesis comprises treatment of 3-hydroxyacetophenone with tosyl chloride to form the tosylated acetophenone, which is thereafter treated with phosphorus oxychloride and DMF to form α-chlorocinnamaldehyde-3-yl(p-toluenesulfonate). Hydrolysis of the latter compound with KOH yields the potassium salt of m-hydroxyphenylacetylene.

Accordingly, it is an object of the present invention to provide a new method for adding terminal acetylene groups to a molecule.

Another object of the present invention is to provide a novel acetylenic end-capping agent for oligomers.

A further object of the present invention is to provide a method for preparing novel acetylenic end-capping agents.

Other objects, aspects and advantages of the present invention will be apparent to those skilled in the art from a reading of the following disclosure.

SUMMARY OF THE INVENTION

In accordance with the present invention there is provided a novel acetylenic end-capping agent having the general formula:

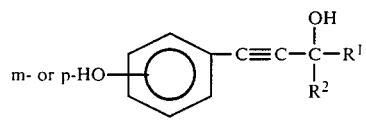

wherein $R^1$ and $R^2$ can be the same or different and are selected from the group consisting of hydrogen, C1 to C4 alkyl, phenyl, and substituted phenyl, and wherein $R^1$ and $R^2$ together with the carbon atom to which they are attached form a saturated 5- or 6-membered ring.

Also provided in accordance with the invention is a method for preparing the above-described acetylenic end-capping agent. The method comprises reacting an m-halophenol with an acetylenic compound of the general formula

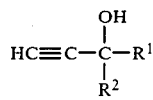

wherein $R^1$ and $R^2$ are as described above, in the presence of a dialkyl or trialkyl amine solvent, a Pd complex catalyst system and a cuprous salt promoter.

Further, in accordance with the present invention, there is provided a method for adding terminal acetylene groups to a molecule which comprises reacting a halogen-terminated molecule with the above-described end-capping agent followed by base-catalyzed cleavage.

DETAILED DESCRIPTION OF THE INVENTION

As stated above, the end-capping agent of the present invention has the general formula

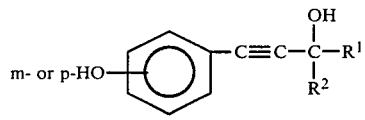

wherein $R^1$ and $R^2$ can be the same as different and are selected from the group consisting of hydrogen, C1 to C4 alkyl, phenyl, substituted phenyl, and wherein $R^1$ and $R^2$ together with the carbon atom to which they are attached form a saturated 5- or 6-membered ring.

The end-capping agent is prepared by reacting a halophenol of the general formula

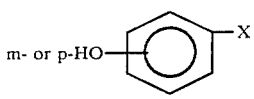

wherein X is —F, —Cl or —Br, with an acetylenic compound of the general formula

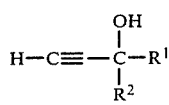

wherein $R^1$ and $R^2$ are as described above, in the presence of a diakyl or trialkyl amine solvent, a Pd complex catalyst system and a cuprous salt promoter. Suitable acetylenic compounds include the following: 2-methyl-3-butyn-2-ol, 3-methyl-1-pentyn-3-ol, 3-ethyl-1-pentyn-3-ol, 2-phenyl-3-butyn-2-ol, 1-ethynylcyclopentanol, and 1-ethynylcyclohexanol. The preparation of these compounds is well known in the art and forms no part of the present invention.

The amine solvent has the formula:

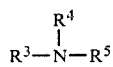

wherein $R^3$, $R^4$ and $R^5$ can be the same or different and are selected from the group consisting of hydrogen and C1–C4 alkyl, with the proviso that no more than one of the R groups can be hydrogen. Suitable solvents include but are not limited to dimethylamine, trimethylamine, diethylamine, triethylamine, dipropylamine, tripropylamine, di-n-butylamine, tri-n-butylamine, ethylpropylamine, and the like, as well as mixtures thereof.

The catalyst employed is a complex palladium salt containing two halogen moieties, wherein the halogen is selected from the group consisting of —Br, —Cl and —I, and two trisubstituted phosphine moieties wherein the constituents are selected from the group consisting of phenyl, C1–C4 alkyl, and substituted phenyl groups. The substituents on the phenyl groups can include C1–C4 alkyl, C1–C4 alkoxy, and halogen. Examples of suitable palladium complex salts include the following: bis(triphenylphosphine)palladium dichloride, bis(triphenylphosphine)palladium dibromide, bis(tri-n-butylphosphine)palladium dichloride, bis(tri-t-butylphosphine)palladium dichloride, bis(tri-i-butylphosphine)palladium dichloride, bis(triethylphosphine)palladium dichloride, bis(tripropylphosphine)palladium dichloride, bis(tritolylphosphine)palladium dichloride, bis(trianisylphosphine)palladium dichloride, bis(tri(chlorophenyl)phosphine)palladium dichloride and bis(tri(bromophenyl)phosphine)palladium dichloride, and the like.

The promoter comprises cuprous salts such as cuprous iodide, cuprous chloride, copper acetylacetonate, cuprous bromide, and the like. Generally, the amount of the promoter is very small, and suitable amounts of promoter include a molar ratio of promoter to palladium catalyst of about 0.5:1 to 20:1, preferably about 1:1 to 5:1. The amount of the palladium catalyst employed in the reaction is about 0.01 to 1.0 mole percent based on the halophenol, preferably about 0.10 to 0.30 mole percent.

It is desirable to include together with the catalyst/promoter system a trisubstituted phosphine, preferably the same trisubstituted phosphine as that which is a part of the complex palladium salt. Generally, the weight ratio of such trisubstituted phosphine to the complex palladium salt can range from about 0.25:1 to 4:1.

The halophenol and the acetylenic compound react to form the end-capping agent of the present invention as follows:

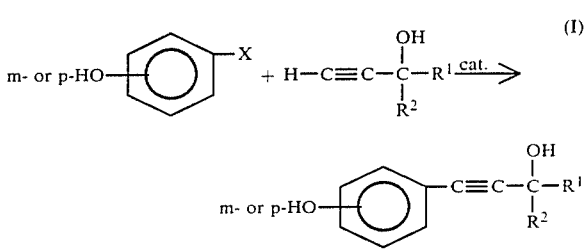

The reaction conditions to employ are relatively mild and include a temperature of about 20° to 200° C., preferably about 50° to 100° C. The reaction conditions should be such that the solvent chosen is maintained in the liquid phase. The normal reaction pressure is atmospheric; however, increased reaction pressures of up to 250 psig (1.7 MPa) or higher may be used. The reaction time to employ is somewhat dependent upon the charge stock and catalyst chosen, as well as the reaction temperature. Generally, the reaction time is from one hour to 150 hours, but usually from about 3 hours to about 30 hours.

The resulting protected ethynylated acetylated phenol is subjected to a metals removal and purification operation for removal of the palladium and copper metal contaminants. A suitable metals removal system involves the use of a combination of a hydrogen halide-treatment step followed by a metals complexing step using an amino compound. The method comprises admixing a solution containing the metal-contaminated acetylated phenol with an aqueous hydrogen halide, e.g., hydrochloric acid, hydrobromic acid, or the like, including mixtures thereof, and then removing the hydrogen halide. Next, the solution is contacted with an amino compound, such as ammonia in the form of ammonium hydroxide, polyamines, such as ethylenediamine, ethylenetriamine, or the like, to form complexes with the metal contaminants, which can be separated from the protected ethynylated phenol by washing the solution with water. The levels of palladium and copper can be reduced to less than 5 ppm.

The metal-contaminated protected ethynylated phenol can be contacted with the hydrogen halide under any suitable conditions, preferably ambient temperature and pressure. Similarly, the acid-treated solution can be contacted with the amino compound to form the metal complexes under any suitable conditions including a temperature in the range of about 40° C. to about 100° C., preferably about 50°–70° C. for a period of about 0.1 to about 2 hours, preferably about 0.25 to 1 hour. Atmospheric or increased pressure can be used as desired.

The protected ethynylated phenols of this invention are useful as end-capping agents for a variety of monomers and oligomers. For example, such compounds can be used for the preparation of thermosetting acetylene-terminated sulfone resins. The sulfones can be prepared according to the general reaction:

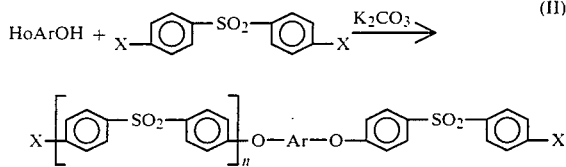

(II)

wherein Ar is a divalent aromatic radical such as

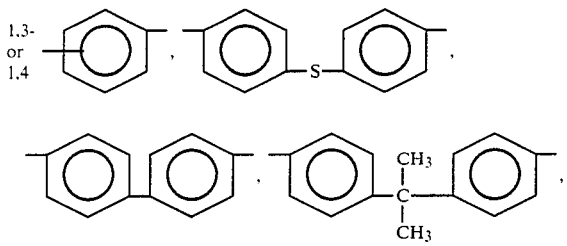

and the like, X is —Cl, —F or —Br, and n is an integer corresponding to the number of recurring units. The value of n can vary within a broad range, e.g., from 1 to about 200.

The phenylenesulfones are well known in the art. They can be readily prepared by the solution condensation of a dialkali metal salt of a dihydric phenol with a dihalo aromatic diphenylsulfone in an anhydrous dipolar aprotic solvent at elevated temperatures. The metal salt may be prepared in situ.

The protected ethynylated phenol end-capping agent of this invention is reacted with a desired molecule in a suitable solvent in the presence of an alkali metal alkoxide. This reaction may be represented as follows:

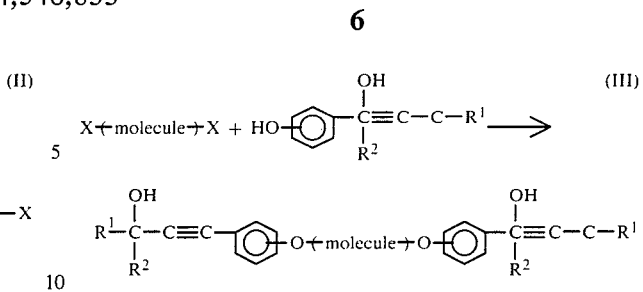

(III)

wherein X, $R^1$ and $R^2$ are as previously described.

Suitable solvents include dimethylsulfoxide, N-methylpyrolidone, bis-methoxy ethoxy diethyl ether, tetrahydrothiophene-1,1-dioxide, and the like. Suitable alkali metal alkoxides include potassium methoxide, potassium ethoxide, cesium ethoxide, and the like.

The reaction of the protected ethynylated phenol with the desired molecule can be conducted under any suitable conditions easily determined by those skilled in the art. The reaction conditions should be such that the solvent chosen is maintained in the liquid phase. The normal reaction pressure is atmospheric; however, increased reaction pressures of up to 250 psig or higher can be employed. Suitable temperatures include those in the range of about 50° to 150° C. The reaction time is somewhat dependent, inter alia, upon the particular charge stock and the reaction temperature. Suitable reaction times include from about 1 to about 50 hours.

The hydroxy-acetylene terminated phenoxy-molecule produced in Reaction (III) is then subjected to base catalyzed cleavage to form the desired acetylene terminated molecule as follows:

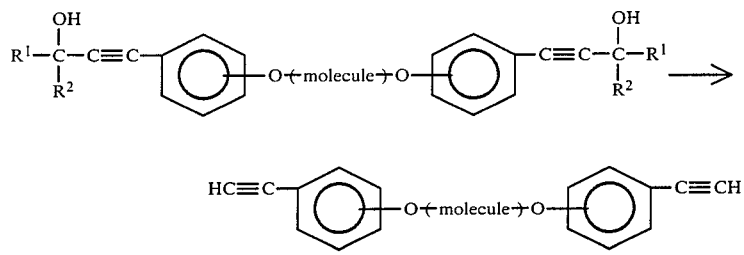

wherein $R^1$ and $R^2$ are as previously defined.

Base catalyzed cleavage is carried out under any suitable reaction conditions, such as a temperature in the approximate range of 50° to 150° C., preferably about 90° to 120° C., in the presence of a suitable base, such as KOH or NaOH, for 0.5 to 20 hours.

Where the desired molecule is a sulfone, as previously described, the above reactions proceed as follows:

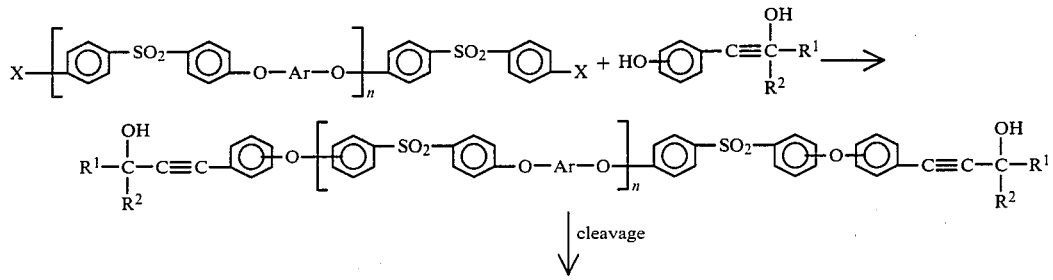

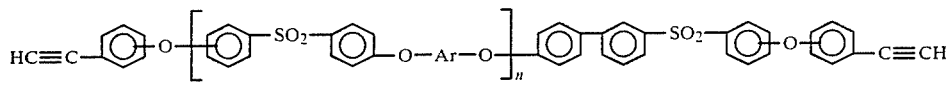

wherein X, n, $R^1$ and $R^2$ are as previously defined.

The protected ethynylated phenol end-capping agents of the present invention may be used to prepare a variety of acetylene terminated monomers and oligomers, including sulfones, as described above, polyimide oligomers, polyarylene oxide oligomers, poly(2,6-benzothiazole)oligomers and the like. Inasmuch as both palladium and copper are removed to very low levels prior to end capping the monomers or oligomers the problem of premature crosslinking due to the presence of these metals is effectively nonexistent.

The following examples illustrate the invention.

EXAMPLE I

Preparation of 3-hydroxyphenyl-2-methyl-3-butyn-2-ol

A 3-necked 500 ml round-bottomed flask was fitted with reflux condenser, magnetic stir bar, stopper, and gas inlet/outlet adapters. Under dry nitrogen the flask was charged with 3-bromophenol (10.0 g, 57.8 mmol), 2-methyl-3-butyn-2-ol (5.0 g, 59.4 mmol) and 250 ml of distilled triethylamine. The mixture was heated at reflux for 15 minutes while nitrogen was bubbled into the solution. To the yellow solution was added dichlorobis(triphenyl)phosphone)palladium II (0.2 g) which was allowed to go completely into solution, triphenylphosphine (0.2 g) and cuprous iodide (0.1 g). The reaction was heated at reflux under nitrogen for 25 h.

After the reaction mixture was cooled to 25° C., using an ice/water bath, it was filtered through a glass frit packed with celite under nitrogen. The remaining light gray ppt was rinsed with additional triethylamine and the fractions combined. The golden yellow filtrate was concentrated (rotary evaporator) and the resulting yellow oil dissolved in 200 ml of toluene and then washed with 120 ml of 8% hydrochloric acid (aqueous). Next the hydrochloric acid washing was extracted with three 50 ml portions of ethyl acetate, the fractions combined, concentrated (rotary evaporator) and dissolved in 25 ml of toluene. The toluene fractions were combined and dried (magnesium sulfate). To the dry toluene solution 50 ml of ethylene diamine was added, turning the solution brown. While bubbling nitrogen through the mixture, the solution was stirred and heated (50°–60° C.) for 15 minutes. During this procedure a blue ppt formed. After cooling to room temperature, the solution was filtered to remove the ppt. The filtrate was next extracted with 250 ml of distilled water and then with three 125 ml portions of 10% potassium carbonate (aqueous). The extract was stirred in an ice/water bath and neutralized with 50% hydrochloric acid (aqueous). The acid addition was continued until the pH was slightly acidic. The aqueous solution was next extracted with one 250 ml portion of ethyl acetate and then three 125 ml portions, dried (magnesium sulfate), filtered and concentrated (rotary evaporator). The resulting dark yellow-orange oil was induced to crystallize by dissolving in methylene chloride, adding n-hexane until slightly cloudy, seeding, and cooling by refrigeration for 24 h. Recrystallizations were repeated until the product was white. The final procedure yielded 4.1 g (41%) of pure product mp: 94°–95° C.

Analysis for $C_{11}H_{12}O_2$: Calc'd: C,74.91; H,6.81. Found: C,74.52; H,6.96.

Analysis for Cu and Pd was found to be less than 3 ppm of each.

EXAMPLE II

Preparation of sulfone monomer and oligomer

A 3-necked, 250 ml, round bottom flask, was equipped with magnetic stir bar, reflux condenser, dean-start trap, and gas inlet/outlet adapters. To the reaction flask the following mixture was added: 4,4'-thiodiphenol (4.0 g, 18.0 mmol), difluorodiphenyl sulfone (18.61 g, 73.0 mmol), anhydrous potassium carbonate (2.53 g, 18.0 mmol), 35 ml of freshly distilled N-methyl-1-pyrrolidone and 30 ml of benzene. The reaction mixture was heated at reflux (100° C.) and stirred rapidly under dry nitrogen until all water (a reaction side product) was essentially removed from the system by azeotropic distillation with benzene. The reaction (light purple in color) temperature was then raised and maintained at 120° C. for 4 h. The mixture darkened slightly during this period. After cooling to 40° C., the reaction mixture was diluted with 100 ml of methylene chloride and washed with three 200 ml portions of 10% hydrochloric acid (aqueous) and one 400 ml portion of distilled water, dried (magnesium sulfate) and filtered. The filtrate was concentrated (rotary evaporator) and chromatographed on a quartz column filled with activated silica gel (500 g). Unreacted difluorodiphenyl sulfone was eluted with n-hexane/chloroform (4/1), the product monomer was eluted with n-hexane/chloroform (1/1) to yield 6.18 g of (I) a white crystalline solid: mp 116°–118° C. The product oligomer was eluted with $ChCl_3$ to yield 5.07 g of (II) a light yellow viscous oil. Total product yield was 11.25 g (89.4%).

Analysis for $C_{36}H_{24}O_6S_3F_2$: Calc'd: C,62.92; H,3.50; S,14.01. Found: C,62.74; H,3.57; S,13.95.

EXAMPLE III

Preparation of Acetylene Terminated Sulfone

A 3-necked, 50 ml round bottom flask was equipped with magnetic stir bar and gas inlet/outlet adapters. Under dry nitrogen the flask was charged with 4-hydroxyphenyl-1-methyl-3-butyn-2-ol (1.63 g, 9.2 mmol) and 40 ml of dimethylsulfoxide. To this solution potassium methoxide (0.65 g, 9.2 mmol) was added. The mixture was stirred for 1 h at 25° C., transferred to an addition funnel under nitrogen, and added over a period of 1 h to a solution of (I) (3 g, 4.4 mmol) in 40 ml of dimethylsulfoxide stirred at 85° C. When addition was complete, the reaction mixture temperature was maintained at 85° C. for an additional 4 hours, after which it was cooled to 25° C. and the mixture stirred overnight under nitrogen. Next the reaction mixture was diluted with 150 ml of methylene chloride and washed with three 300 ml portions of 10% hydrochloric acid (aqueous) dried (magnesium sulfate) and filtered. The filtrate was concentrated (by rotary evaporator) and chromatographed on a quartz column filled with activated silica gel (180 g). The product was eluted with ethyl acetate/chloroform (1/9) to yield 3.16 g (68.7%) of (III) a white solid: mp 156°–157° C.

Analysis for $C_{58}H_{46}O_{10}S_3$: Calc'd: C,69.68; H,4.61; S,9.63. Found: C,67.33; H,4.64; S,9.26.

While heating under nitrogen (III) (2.0 g, 2.0 mmol) was dissolved in 60 ml of dry benzene contained in a 3-necked, 250 ml round bottomed flask. The reaction flask was equipped with a dean-stark trap, reflux condenser, magnetic stir bar and gas inlet/outlet adapters. After (III) was observed to go completely into solution, 50 ml of 10% methanolic potassium hydroxide was added and the mixture stirred and heated at reflux for 1 h. Acetone formed as the reaction progressed and was removed from the system along with half of the original volume of benzene. The lost volume of benzene was replaced and the distillation procedure repeated three more times (replacing the lost volume of benzene the first and second times). The progress of the reaction was followed by TLC on silica gel with methylene chloride. After 4 h, the reaction mixture was cooled to 25° C., filtered over celite and washed with three 100 ml portions of distilled water, dried (magnesium sulfate) and filtered. The filtrate was concentrated (rotary evaporator) and chromatographed on a quartz column filled with activated silica gel (160 g). The product was eluted with hexane/chloroform (1/1) to yield 1.39 g (79%) of (IV) a fluffy white solid: mp 91°–94° C.

Analysis for $C_{25}H_{34}O_8S_2$: (Monomer) Calc'd: C,70.69; H,3.85; S,10.89. Found: C,69.39; H,3.95; S,10.75.

Product IV had an initial Tg of 45° C., as determined by DSC (10° C./min) and, following curing at 550° F. for 8 hours, a cured Tg of 232° C., as determined by TMA (10° C./min).

We claim:
1. A method for preparing a compound of the formula

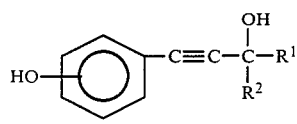

wherein $R^1$ and $R^2$ are the same or different and are selected from the group consisting of hydrogen, C1 to C4 alkyl, phenyl and substituted phenyl, and wherein $R^1$ and $R^2$ together with the carbon atom to which they are attached form a saturated 5- or 6-membered ring, which comprises the steps of reacting a halophenol of the formula

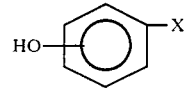

wherein X is —F, —Cl or —Br, with an acetylenic compound of the formula

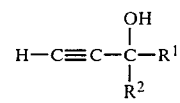

wherein $R^1$ and $R^2$ are as defined above, in the presence of an amine solvent, a catalytic amount of a palladium complex catalyst system and a promoting amount of a cuprous salt promoter under reaction conditions, and recovering the resulting protected ethynylated phenol compound wherein said reaction conditions include a temperature of about 20° to 200° C., a reaction pressure of atmospheric up to about 250 psig, and a reaction time of about 1 to 150 hours.

2. The method of claim 1 wherein said recovering step includes removal of palladium and copper to less than 5 ppm.

3. The method of claim 2 wherein said removal step comprises contacting a solution containing the metal-contaminated ethynylated phenol compound with an aqueous hydrogen halide, removing the hydrogen halide, contacting the resulting solution with an amino compound capable of complexing with said Pd and said Cu, and separating the resulting complexed Pd and Cu from the solution containing said ethynylated phenol compound.

4. A method for producing an acetylene terminated compound which comprises reacting, under reaction conditions, a halogen-terminated compound selected from the group consisting of sulfones, polyimide oligomers, polyarylene oxide oligomers and poly(2,6-benzothiazole) oligomers with a compound of the formula

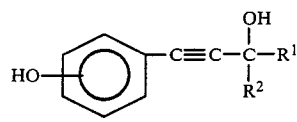

wherein $R^1$ and $R^2$ are the same or different and are selected from the group consisting of hydrogen, C1 to C4 alkyl, phenyl, and substituted phenyl, and wherein $R^1$ and $R^2$ together with the carbon atom to which they are attached form a saturated 5- or 6-membered ring, to form an intermediate product, and cleaving said intermediate product with a suitable base to form said acetylene-terminated compound wherein said reaction conditions include a temperature of about 50° to 150° C., a reaction pressure of atmospheric up to about 250 psig, and a reaction time of about 1 to 50 hours.

5. The method of claim 4 wherein said halogen-terminated molecule is a dihalosulfone.

* * * * *